United States Patent [19]

Abdulla

[11] 4,127,581
[45] Nov. 28, 1978

[54] METHOD FOR THE PREPARATION OF 3-PHENYL-5-SUBSTITUTED-4(1H)-PYRIDONES

[75] Inventor: Riaz F. Abdulla, Greenfield, Ind.

[73] Assignee: Eli Lilly and Company, Indianapolis, Ind.

[21] Appl. No.: 831,455

[22] Filed: Sep. 8, 1977

[51] Int. Cl.² ............................................ C07D 213/04
[52] U.S. Cl. ..................................... 546/250; 546/296; 542/455
[58] Field of Search ................... 260/297 Z, 294.8 F, 260/294.8 G, 294.9, 295 R, 293.69; 544/124

[56] References Cited

U.S. PATENT DOCUMENTS 4,065,290  12/1977  Taylor ........................ 260/290 HL Primary Examiner—Alan L. Rotman
Attorney, Agent, or Firm—Leroy Whitaker; Arthur R. Whale

[57] ABSTRACT

A class of herbicidal 3-phenyl-5-substituted-4(1H)-pyridones are prepared from β-aminostyrenes by reaction with bromoacetyl bromide to form an α-bromoacetyl-β-aminostyrene which is reacted with an anion to form a α-substituted acetyl-β-aminostyrene which is then cyclized to the pyridone by formylation and reaction with a primary amine.

6 Claims, No Drawings

METHOD FOR THE PREPARATION OF 3-PHENYL-5-SUBSTITUTED-4(1H)-PYRIDONES

BACKGROUND OF THE INVENTION

Belgian Pat. No. 832702 describes a class of 3-phenyl-5-substituted-4(1H)-pyridones which are broad spectrum herbicides. Included within the scope of the Belgian disclosure are many of the compounds prepared by the presently claimed process. The Belgian patent describes a process for the preparation of the pyridones which involves the same final step as the present process, i.e., the formation of the pyridone ring by formylation of an α-substituted acetyl-β-aminostyrene followed by reaction with a primary amine. However, the present process differs markedly from that of the Belgian patent in the steps leading to the intermediate α-substituted acetyl-β-aminostyrene.

Another of the steps of the present process, the reaction of bromoacetyl bromide with a β-aminostyrene, is disclosed by Garcia et al., *J. Heterocyclic Chem.*, 11, 219 (1974). Garcia's objective was the preparation of substituted indoles by way of o-nitrobenzylketones. There is no suggestion by Garcia et al., of the preparation of pyridones as described herein.

SUMMARY OF THE INVENTION

I have now discovered a method for the preparation of a substituted pyridone having the formula

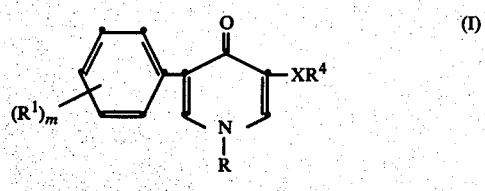

which comprises:
(a) treating an enamine having the formula

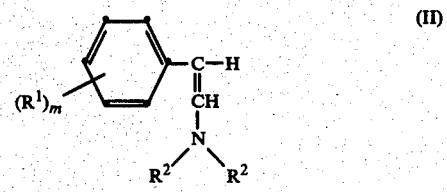

with bromoacetyl bromide in the presence of an acid scavenger in an inert solvent at a temperature of from about −25° C. to about 50° C. to form an α-bromoacetyl-β-aminostyrene having the formula

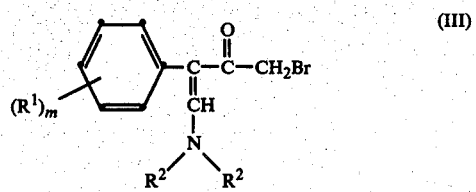

(b) treating the α-bromoacetyl-β-aminostyrene with an anion represented by

 $XR^4$ (IV)

in an inert solvent at a temperature of from about 0° C. to about 100° C. to give an α-substituted acetyl-β-aminostyrene having the formula

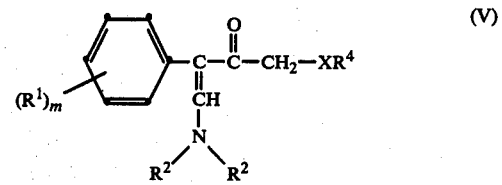

(c) formylating or aminoformylating the α-substituted acetyl-β-aminostyrene by treatment with
  (1) a $C_1$-$C_2$ alkyl formate and an alkali metal $C_1$-$C_2$ alkoxide in an aprotic solvent at a temperature of from about −25° C. to about 25° C., or
  (2) an N,N-dimethylformamide acetal at a temperature within the range of from about 50° C. to about 150° C., and treating with an amine, $RNH_2$, in a protic solvent at a temperature of from about −20° C. to about 100° C. to produce the substituted pyridone;

wherein R represents
  $C_1$-$C_3$ alkyl,
  $C_1$-$C_3$ alkyl substituted with halo, cyano, carboxy, or methoxycarbonyl,
  $C_2$-$C_3$ alkenyl,
  $C_2$-$C_3$ alkynyl,
  $C_1$-$C_3$ alkoxy,
  acetoxy, or
  dimethylamino,
provided that R comprises no more than 3 carbon atoms; each $R^1$ independently represents
  halo,
  $C_1$-$C_8$ alkyl,
  $C_1$-$C_8$ alkyl substituted with halo,
  $C_1$-$C_8$ alkyl monosubstituted with phenyl, cyano, or $C_1$-$C_3$ alkoxy,
  $C_2$-$C_8$ alkenyl,
  $C_2$-$C_8$ alkenyl substituted with halo,
  $C_2$-$C_8$ alkynyl,
  $C_2$-$C_8$ alkynyl substituted with halo,
  $C_3$-$C_6$ cycloalkyl,
  $C_4$-$C_6$ cycloalkenyl,
  $C_4$-$C_8$ cycloalkylalkyl,
  $C_1$-$C_3$ alkanoyloxy,
  $C_1$-$C_3$ alkylsulfonyloxy,
  phenyl,
  phenyl monosubstituted with halo, $C_1$-$C_3$ alkyl, $C_1$-$C_3$ alkoxy, or nitro,
  nitro,
  cyano,
  carboxy,
  hydroxy,
  $C_1$-$C_3$ alkoxycarbonyl,
  —O—$R^3$,
  —S—$R^3$,
  —SO—$R^3$, or
  —$SO_2$—$R^3$;
$R^3$ represents
  $C_1$-$C_{12}$ alkyl,
  $C_1$-$C_{12}$ alkyl substituted with halo,
  $C_1$-$C_{12}$ alkyl monosubstituted with phenyl, cyano, or $C_1$-$C_3$ alkoxy,
  phenyl, phenyl monosubstituted with halo, $C_1$-$C_3$ alkyl, $C_1$-$C_3$ alkoxy or nitro,
$C_3$-$C_6$ cycloalkyl,
$C_4$-$C_8$ cycloalkylalkyl,
$C_2$-$C_{12}$ alkenyl,
$C_2$-$C_{12}$ alkenyl substituted with halo,
$C_2$-$C_{12}$ alkynyl,
$C_2$-$C_{12}$ alkynyl substituted with halo, provided that $R^3$ comprises no more than 12 carbon atoms; each $R^2$ independently represents $C_1$-$C_4$ alkyl or both $R^2$ groups taken together with the nitrogen atom to which they are attached represent
pyrrolidino,
piperidino, or
morpholino;
$R^4$ represents
$C_1$-$C_6$ alkyl,
$C_1$-$C_6$ alkyl substituted with halo,
$C_1$-$C_6$ alkyl mono- or disubstituted with hydroxy,
$CH_2R^5$,
benzyl,
phenyl or
phenyl substituted with halo, $C_1$-$C_3$ alkyl, halo $C_1$-$C_3$ alkyl or $C_1$-$C_3$ alkoxy;
$R^5$ represents
$C_2$-$C_5$ alkenyl,
$C_2$-$C_5$ alkenyl substituted with halo or
$C_2$-$C_5$ alkynyl; X represents oxygen or sulfur; and $m$ represents 0, 1 or 2.

DESCRIPTION OF THE PREFERRED EMBODIMENT

In the above description of my process, the chemical terms used have their normal meanings. For example, the various alkyl, alkenyl, alkynyl and alkoxy terms refer to both straight and branched chain groups and include such exemplary groups as methyl, ethyl, isopropyl, vinyl, allyl, methoxy, isopropoxy, propargyl, isobutyl, hexyl, octyl, 1,1-dimethylpentyl, 2-octenyl, pentyl, 3-hexynyl, 1-ethyl-2-hexenyl, 3-octynyl, 5-heptenyl, 1-propyl-3-butynyl and crotyl.

The terms $C_3$-$C_6$ cycloalkyl and $C_4$-$C_6$ cycloalkenyl refer to such groups as cyclopropyl, cyclobutyl, cyclohexyl, cyclobutenyl, cyclopentenyl and cyclohexadienyl.

The term $C_4$-$C_8$ cycloalkylalkyl refers to such groups as cyclopropylmethyl, cyclobutylmethyl, cyclohexylmethyl, and cyclohexylethyl.

The term $C_1$-$C_3$ alkanoyloxy refers to groups such as formyloxy, acetoxy and propionyloxy.

The term $C_1$-$C_3$ alkoxycarbonyl refers to groups such as methoxycarbonyl, ethoxycarbonyl, and isopropoxycarbonyl.

The term $C_1$-$C_3$ alkylsulfonyloxy refers to such groups as methylsulfonyloxy and propylsulfonyloxy.

The term halo refers to fluoro, chloro, bromo, and iodo.

The present process is preferably used in the preparation of compounds of Formula I wherein $R^1$ is 3-trifluoromethyl, X is sulfur, and $R^4$ is a lower alkyl group, especially ethyl. The most preferred compounds are those in which R is methyl.

The starting materials for the present process are enamines of Formula II. Such enamines are conveniently obtained from phenylacetaldehydes and dialkylamines via the method of Mannich et al., Chem. Ber. 69, 2106 (1936).

The enamine is then reacted with bromoacetyl bromide in the presence of an acid scavenger to neutralize the hydrogen bromide formed in the reaction. The use of acid scavengers in this manner is well known in the art. Acid scavengers are basic compounds which will neutralize the hydrogen bromide. The most suitable acid scavengers for use in the process are tertiary amines such as pyridine or triethylamine; however, anhydrous potassium carbonate may also be used.

The reaction of the enamine with bromoacetyl bromide is conducted at a temperature of from about $-25°$ C. to about 25° C. preferably from about $-10°$ C. to about 10° C. in an inert solvent. Ethers are especially useful as solvents for the reaction. Suitable ethers include, for example, diethyl ether, ethylene glycol dimethyl ether, tetrahydrofuran, and, at the upper end of the temperature range, dioxane.

In the second step of the process, the α-bromoacetyl-β-aminostyrene obtained in the first step is treated with an anion in an inert solvent at a temperature of from about 0° C. to about 100° C. to give an α-substituted acetyl-β-aminostyrene. The anion represented by $(-)XR^4$ displaces the bromine from the α-bromoacetyl-β-aminostyrene, surprisingly without decomposition of the enamine. The anion is introduced into the reaction mixture as a metallic salt, preferably an alkali metal salt.

It is well known in the art to prepare the anions $(-)XR^4$. Such anions are conveniently prepared as alkali metal salts, preferably sodium or lithium salts. The sodium salts may be generated from metallic sodium or in some instances from sodium alkoxides. Lithium salts are conveniently obtained by treating a compound of the formula $HXR^4$ with an alkyllithium such as n-butyllithium.

The solvent employed in the second step of the reaction is one that does not interfere with the displacement of the bromine by the anion. Among such solvents are ethers, such as diethyl ether and tetrahydrofuran, or hydrocarbons such as benzene and toluene. The lower alkanols may also be used, especially when the anion is the corresponding alkoxide ion. This reaction is conducted at a temperature of from about 0° C. to about 100° C. The reaction is complete within from about 1 to about 24 hours.

In the third step of the reaction, the α-substituted acetyl-β-aminostyrene having Formula V is formylated and reacted with an amine, $RNH_2$, but not necessarily in that order. The reaction with the amine may precede the formylation. No matter whether the formylation or reaction with the amine comes first, the result is cyclization to the pyridone having Formula I.

The term "formylation" is used broadly to denote either formylation or aminoformylation. Formylation is accomplished by treatment with a $C_1$-$C_2$ alkyl formate and an alkali metal $C_1$-$C_2$ alkoxide to produce a compound of Formula VI

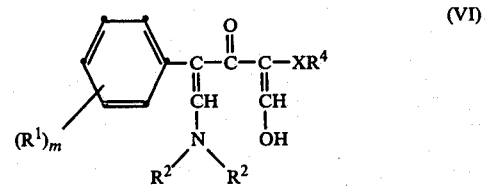

Alternatively, the α-substituted acetyl-β-aminostyrene from the second step of the process may be aminoformylated by treatment with an N,N-dimethylformamide acetal to yield an intermediate compound of Formula VII

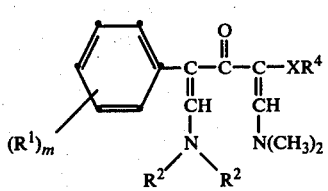

It is understood that the N,N-dimethylformamide acetal may be replaced by other N,N-disubstitutedformamide acetals such as the diethyl or one in which the nitrogen forms a part of a ring. The acetal portion is preferably the dimethyl or diethyl acetal, but may also be a cyclic acetal, such as that formed from ethylene glycol.

Formylating and aminoformylating agents have been extensively described in the chemical literature. Numerous such agents are known and are equivalent to the alkyl formate and alkali metal alkoxide or N,N-dimethylformamide acetal described herein.

Formylation reactions are performed in aprotic solvents including ethers, such as diethyl ether, 1,2-dimethoxyethane, and tetrahydrofuran, and hydrocarbon solvents, such as benzene, toluene, xylene, hexane, and octane. Because of the strong bases used in the formylation reaction, low temperatures in the range of from about −25° C. to about 25° C. generally result in the best yields. After the reaction has proceeded part way to completion, the reaction may be allowed to warm slightly. Reaction times of from about 1 to about 24 hours are sufficient.

Aminoformylation reactions are usually carried out without a solvent at elevated temperatures of from about 50° C. to about 150° C. Sometimes a solvent such as dimethylformamide may be used, particularly when it is desirable to raise the boiling point of the reaction mixture. It is well known, however, that the use of certain aminoformylating agents, such as formiminium halides, is best conducted in an aprotic solvent at a temperature of from about 0° C. to 50° C.

The reaction with the amine, $RNH_2$, is best performed in a protic solvent at a temperature of from about −20° C. to 100° C. Examples of protic solvents are the alkanols, of which ethanol is preferred.

If the formylation or aminoformylation has been performed prior to treatment with the amine, $RNH_2$, ring closure occurs and the pyridone is formed. However, treatment with the amine may be done prior to the formylation or aminoformylation in which case there is displacement of the amino group present in the α-substituted acetyl-β-aminostyrene to give a compound of Formula VIII

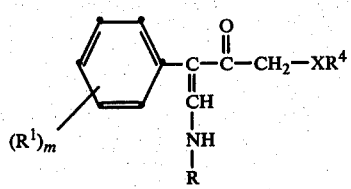

The intermediate compound VIII is then formylated or aminoformylated to yield the pyridone.

The intermediate compounds, VI, VII, and VIII generally are not isolated but are subjected to subsequent treatment to yield the desired pyridone.

It is understood that those pyridones wherein X is sulfur may be oxidized to obtain the corresponding sulfoxides and sulfones. Such subsequent reactions do not form a part of the present process.

The claimed process will be illustrated by the following examples which are not to be interpreted as limiting the scope of the process. In general, intermediate compounds of Formula V were oils which did not solidify. They were characterized by IR and NMR spectra and used in subsequent steps of the process. Examples 1 and 2 illustrate the preparation of the α-bromoacetyl-β-aminostyrene intermediates of Formula III, by reaction of an enamine with bromoacetyl bromide. The other steps in the process are illustrated by the further examples.

EXAMPLE 1

α-Bromoacetyl-β-diethylaminostyrene

To a solution of 17.5 g. of diethylstyrylamine in 200 ml. of ether was added 8.5 g. of pyridine. The mixture was cooled to 5° C. and a solution of 20.1 g. of bromoacetyl bromide in 200 ml. of ether was added over a period of about 4 hours. The mixture was filtered and the residue on the filter was washed with 300 ml. of ether. The combined ether filtrate and washings was washed with 1 N hydrochloric acid, 0.1 N sodium hydroxide, saturated aqueous sodium chloride, and dried over magnesium sulfate and activated carbon. The mixture was filtered and the ether was evaporated to give a quantitative yield of α-bromoacetyl-β-diethylaminostyrene. The product was shown by NMR spectrum to be a mixture of the cis and trans isomers.

EXAMPLE 2

α-Bromoacetyl-β-diethylamino-3-trifluoromethylstyrene

To a solution of 12.1 g. of N,N-diethyl-3-trifluoromethylstyrylamine and 4.5 g. of pyridine in 200 ml. of ether was added a solution of 10.0 g. of bromoacetyl bromide in 200 ml. of ether over a period of about 2 hours. The mixture was filtered and the filtrate was washed with 1 N hydrochloric acid, 0.1 N sodium hydroxide, saturated sodium chloride, and dried over magnesium sulfate.

The mixture was again filtered, and the ether was evaporated to give a quantitative yield of α-bromoacetyl-β-diethylamino-3-trifluoromethylstyrene.

Analysis calc. for $C_{15}H_{17}NOBrF_3$: C, 49.45; H, 4.67; N, 3.85. Found: C, 49.33; H, 4.07; N, 3.69.

EXAMPLE 3

3-Ethylthio-1-methyl-5-(α,α,α-trifluoro-m-tolyl)-4(1H)-pyridone

To 10 ml. of anhydrous tetrahydrofuran at −20° C. were added 1.3 g. of ethanethiol and 13 ml. of 1.6 M n-butyllithium solution and the mixture was stirred under nitrogen for 15 minutes. The solution was allowed to warm to room temperature and a solution of 7.24 g. of α-bromoacetyl-β-diethylamino-3-trifluoromethylstyrene in 10 ml. of tetrahydrofuran was added. The mixture was stirred and heated under reflux overnight. The tetrahydrofuran was stripped off to leave an oil which was dissolved in chloroform and the solution was washed with 1 N hydrochloric acid, 0.1 N sodium hydroxide and saturated sodium chloride. Removal of the chloroform left an oil. One gram of this oil was removed and the remainder was heated under reflux with 25 ml. of N,N-dimethylformamide dimethylacetal for 3 days. The excess dimethylformamide acetal was stripped off and a solution of 5.0 grams of methylamine hydrochloride in 50 ml. of ethanol was added. This solution was heated under reflux for 24 hours. The reaction was poured into methylene chloride and the resulting solution was washed with 1 N hydrochloric acid, 1 N sodium hydroxide and saturated sodium chloride, then dried over magnesium sulfate, filtered, and the solvent stripped. The residue was triturated under diisopropyl ether to give crystalline 3-ethylthio-1-methyl-5-($\alpha,\alpha,\alpha$-trifluoro-m-tolyl)-4(1H)-pyridone, m.p. 84°–85° C. The overall yield was 2.5 g. (40%).

EXAMPLE 4

1-Methyl-5-(3-trifluoromethylphenyl)-3-trifluoromethylthio-4(1H)-pyridone

A mixture of 7.28 g. of $\alpha$-bromoacetyl-$\beta$-diethylamino-3-trifluoromethylstyrene and 5.64 g. of the cuprous salt of trifluoromethyl mercaptan in 100 ml. of dry acetonitrile was stirred overnight under nitrogen at a temperature of 60°–70° C. The mixture was cooled, filtered and evaporated in vacuo. The residue was taken up in methylene chloride, the solution filtered, washed with water and dried over magnesium sulfate. Evaporation of the methylene chloride in vacuo left an oil which was used without further purification. To the oil was added 50 ml. of dimethylformamide diethylacetal and the mixture was heated under reflux overnight. The excess acetal was removed in vacuo and the residual oil was taken up in 2B ethanol. To the solution was added 10.0 g. of methylamine hydrochloride and the mixture was heated under reflux overnight. The solution was cooled, filtered and evaporated in vacuo. The dark residue was taken up in methylene chloride and the solution washed with water and saturated sodium chloride solution and dried over magnesium sulfate. Evaporation of the solvent left a dark oil which was chromatographed on silica gel using first benzene, followed by benzene containing 10% ethyl acetate, then benzene containing 20% ethyl acetate. The desired product was removed from the column in the 20% ethyl acetate solvent. The solvent was evaporated and the residual oil was triturated in hexane causing it to crystallize. Recrystallization from hexane-methylene chloride yielded 1.5 g. (21%) of 1-methyl-5-(3-trifluoromethylphenyl)-3-trifluoromethylthio-4(1H)-pyridone, m.p. 122°–124° C.

Analysis calculated for $C_{14}H_9F_6NOS$: C, 47.60; H, 2.57; N, 3.96. Found: C, 47.83; H, 2.43; N, 4.00.

EXAMPLE 5

3-t-Butylthio-5-(4-chloro-3-trifluoromethylphenyl)-1-methyl-4(1H)-pyridone

To 4.6 ml. of t-butyl mercaptan in 250 ml. of methanol was added with stirring 2.16 g. of sodium methylate. Over a period of 15 minutes, a solution of 16.0 g. of $\alpha$-bromoacetyl-4-chloro-$\beta$-diethylamino-3-trifluoromethylstyrene in 50 ml. of methanol was added. After addition was complete, the mixture was heated under reflux for 6 hours. The mixture was allowed to cool and the solvent was removed by stripping. The residue was taken up in 250 ml. of methylene chloride and the solution was washed with 1 N hydrochloric acid, 1 N sodium hydroxide and saturated sodium chloride. The solution was then dried over magnesium sulfate, filtered and the solvent removed by stripping. The dark oil was used without further purification. The oil was dissolved in 200 ml. of dry tetrahydrofuran, and to the solution was added with stirring 35 ml. of 40% aqueous methylamine. After stirring at room temperature for 3½ hours, the solvent was removed from the mixture by stripping. The residue was taken up in methylene chloride and the solution washed with 1 N hydrochloric acid and saturated sodium chloride and was then dried over magnesium sulfate. The solution was filtered and the solvent stripped to leave a dark oil. The oil was dissolved in 50 ml. of toluene and 9 ml. of dimethylformamide dimethylacetal was added. The mixture was stirred and heated under reflux overnight. After cooling, the solvent was removed by stripping and 200 ml. of diisopropyl ether was added. When no crystals formed, the material was put over a silica gel column using methylene dichloride as the eluting solvent. No product was obtained using methylene dichloride so methylene dichloride containing 10% ethyl acetate was used as eluting solvent. Evaporation of the methylene dichloride/ethyl acetate left a residue which was one spot material on thin-layer chromatography. This residue was taken up in diisopropyl ether and with stirring a light tan solid precipitated. There obtained 4.0 g. (26.7%) of 3-t-butylthio-5-(4-chloro-3-trifluoromethylphenyl)-1-methyl-4(1H)-pyridone, m.p. 138°–142° C.

Analysis calculated for $C_{17}H_{17}NOClF_3S$: C, 54.33; H, 4.56; N, 3.73. Found: C, 54.44; H, 4.35; N, 3.46.

EXAMPLE 6

3-Methoxy-1-methyl-5-phenyl-4(1H)-pyridone

To 1.5 g. of $\alpha$-bromoacetyl-$\beta$-diethylaminostyrene in 10 ml. of anhydrous methanol stirred at 50° C. was added dropwise a solution of 0.26 g. of sodium methoxide in 10 ml. of anhydrous methanol. The addition required about 3 minutes. After addition was complete, the mixture was stirred at 70° C. for 4 hours. The solvent was evaporated and the residue was taken up in methylene chloride and washed with 1 N hydrochloric acid, 1 N sodium hydroxide, saturated sodium chloride solution and then dried. Evaporation of the methylene chloride left a an oily residue identified as $\beta$-diethylamino-$\alpha$-methoxyacetylstyrene.

About 5 g. of $\beta$-diethylamino-$\alpha$-methoxyacetylstyrene was mixed with 3.2 g. of sodium methoxide in 50 ml. of dry tetrahydrofuran at 0° C. and 4.4 g. of ethyl formate was added dropwise. The mixture was stirred for 3 hours, and 25 ml. of 40% aqueous methylamine was added followed by 5 g. of methylamine hydrochloride. The mixture was stirred overnight at room temperature and the solvents were removed under vacuum. The residue was taken up in methylene chloride, washed with water and saturated sodium chloride solution and dried. The solvent was removed under vacuum and the residue was triturated with diethyl ether. Recrystallization of the solids from diisopropyl ether/methylene chloride gave 1 g. of 3-methoxy-1-methyl-5-phenyl-4(1H)-pyridone, m.p. 153°–155° C.

EXAMPLE 7

1-Methyl-3-(n-pentylthio)-5-(3-trifluoromethylphenyl)-4(1H)-pyridone

To a stirred solution of 2.6 ml. of 1-pentanethiol in 50 ml. of anhydrous methanol was added 1.08 g. of sodium methylate and the mixture was stirred for 15 minutes. To the solution was added 7.24 g. of α-bromoacetyl-β-diethylamino-3-trifluoromethylstyrene in 50 ml. of anhydrous methanol. The mixture was heated under reflux for 4 hours. After cooling to 30° C., a solution of 25 ml. of 40% methylamine and 25 ml. of methanol was added and the mixture was stirred at room temperature overnight. The solvent was removed by stripping, the residue was taken up in ether and the ether solution was successively washed with 1 N hydrochloric acid, 1 N sodium hydroxide and a saturated sodium chloride solution. After drying over magnesium sulfate, the mixture was filtered and the solvent was removed by stripping. The residue was dissolved in 25 ml. of anhydrous toluene, 4.5 ml. of dimethylformamide dimethylacetal was added and the mixture was heated under gentle reflux overnight. After removal of the solvent, the residue was triturated under 200 ml. of diisopropyl ether to give a light tan solid which was recovered by filtration. There was obtained 2.2 g. of 1-methyl-3-n-pentylthio-5-(3-trifluoromethylphenyl)-4(1H)-pyridone, m.p. 89°–92° C.

Analysis calculated for $C_{18}H_{20}NOF_3S$: C, 60.83; H, 5.67; N, 3.94. Found: C, 60.73; H, 5.67; N, 3.72.

EXAMPLE 8

3-sec-Butylthio-1-methyl-5-(3-trifluoromethylphenyl)-4(1H)-pyridone

To a solution of 2.0 g. of 2-butanethiol in 25 ml. of anhydrous tetrahydrofuran was added 8.0 ml. of 2.5 M n-butyllithium at 20° C. Upon addition, an exotherm occurred and the temperature of the solution increased. After 5 minutes, a solution of 7.24 g. of α-bromoacetyl-β-diethylamino-3-trifluoromethylstyrene in 15 ml. of anhydrous tetrahydrofuran was added and the mixture was heated under reflux for 16 hours. The solvent was removed, the residue was taken up in chloroform and the solution was successively washed with 1 N hydrochloric acid, 1 N sodium hydroxide and water. After drying, the solvent was removed and the residue was dissolved in 30 ml. of N,N-dimethylformamide dimethylacetal and the mixture was heated under reflux for 3 days. Excess acetal was removed by stripping and the resulting oil was dissolved in 100 ml. of 2B ethanol and 8.0 g. of methylamine hydrochloride was added. The mixture was heated under reflux under nitrogen for 24 hours. Workup of the mixture yielded 2.2 g. of 3-sec-butylthio-1-methyl-5-(3-trifluoromethylphenyl)-4(1H)-pyridone as a viscous oil which did not solidify.

Following the procedures described in detail in the above examples, the following additional compounds were prepared by the process of this invention.

EXAMPLE 9

3-Methyllylthio-1-methyl-5-(3-trifluoromethylphenyl)-4(1H)-pyridone, 1.28 g. from 12.0 g. of α-bromoacetyl-β-diethylamino-3-trifluoromethylstyrene and 2.9 g. of methallyl mercaptan. m.p. 86°–88° C.

Analysis calculated for $C_{17}H_{16}NOSF_3$: C, 60.18; H, 4.72; N, 4.13. Found: C, 60.21; H, 4.77; N, 3.88.

EXAMPLE 10

3-(2-Hydroxy-1-propylthio)-1-methyl-5-(3-trifluoromethylphenyl)-4(1H)-pyridone, 1.0 g. from 12.0 g. of α-bromoacetyl-β-diethylamino-3-trifluoromethylstyrene and 3.05 g. of 1-mercapto-2-propanol, m.p. 99°–102° C.

Analysis calculated for $C_{16}H_{16}NO_2SF_3$: C, 55.97; H, 4.70; N, 4.08. Found: C, 56.08; H, 4.74; N, 4.20.

EXAMPLE 11

3-(1,1-Dimethylpropylthio)-1-methyl-5-(3-trifluoromethylphenyl)-4(1H)-pyridone, 0.05 gram from 7.24 grams of α-bromoacetyl-β-diethylamino-3-trifluoromethylstyrene and 2.6 ml. of 2-methyl-2-butanethiol, m.p. 88°–90° C.

Analysis calculated for $C_{18}H_{20}NOSF_3$: C, 60.83; H, 5.67; N, 3.94. Found: C, 60.62; H, 5.63; N, 3.66.

EXAMPLE 12

3-(2-Hydroxyethylthio)-1-methyl-5-(3-trifluoromethylphenyl)-4(1H)-pyridone, 4.25 grams from 24 grams of α-bromoacetyl-β-diethylamino-3-trifluoromethylstyrene and 5.2 grams of 2-mercaptoethanol, m.p. 116°–118° C.

EXAMPLE 13

3-(3-Methyl-2-butylthio)-1-methyl-5-(3-trifluoromethylphenyl)-4(1H)-pyridone, 3.01 grams from 7.24 grams of α-bromoacetyl-β-diethylamino-3-trifluoromethylstyrene and 2.6 ml. of 3-methyl-2-butyl mercaptan, amber oil which did not crystallize.

EXAMPLE 14

3-Allylthio-1-methyl-5-(3-trifluoromethylphenyl)-4(1H)-pyridone, 0.6 grams from 7.24 grams of α-bromoacetyl-β-diethylamino-3-trifluoromethylstyrene and 2.5 grams of allyl mercaptan, m.p. 74°–75° C.

EXAMPLE 15

3-Allylthio-1-methyl-5-phenyl-4(1H)-pyridone, 1.0 gram from 5.9 grams of α-bromoacetyl-β-diethylaminostyrene and 2.26 grams of 70% allyl mercaptan, m.p. 136°–138° C.

EXAMPLE 16

3-Isopropylthio-1-methyl-5-(4-chloro-3-trifluoromethylphenyl)-4(1H)-pyridone, 1.90 gram from 7.95 grams of α-bromoacetyl-β-diethylamino-4-chloro-3-trifluoromethylstyrene and 2.0 grams of 2-propanethiol, m.p. 127°–129° C.

EXAMPLE 17

3-(n-Propylthio)-1-methyl-5-(4-chloro-3-trifluoromethylphenyl)-4(1H)-pyridone, 1.65 grams from 7.95 grams of α-bromoacetyl-β-diethylamino-4-chloro-3-trifluoromethylstyrene and 2.0 grams of n-propanethiol, m.p. 128°–130° C.

EXAMPLE 18

3-Isobutylthio-1-methyl-5-(3-trifluoromethylphenyl)-4(1H)-pyridone, from α-bromoacetyl-β-diethylamino-3-trifluoromethylstyrene and 2-methyl-1-propanethiol, m.p. 106°–107° C.

EXAMPLE 19

3-t-Butylthio-1-methyl-5-(3-trifluoromethylphenyl)-4(1H)-pyridone, 2.00 grams from 7.24 grams of α-bromoacetyl-β-diethylamino-3-trifluoromethylstyrene and 2.0 grams of 2-methyl-2-propanethiol, m.p. 124°–125° C.

EXAMPLE 20

3-Ethylthio-1-methyl-5-(4-chloro-3-trifluoromethylphenyl)-4(1H)-pyridone, 0.75 gram from 7.95 grams of α-bromoacetyl-β-diethylamino-4-chloro-3-trifluoromethylstyrene and 1.5 grams of ethanethiol, m.p. 115°–116° C.

EXAMPLE 21

3-(2,3-Dihydroxy-1-propylthio)-1-methyl-5-(3-trifluoromethylphenyl)-4(1H)-pyridone, 0.43 gram from 7.24 grams of α-bromoacetyl-β-diethylamino-3-trifluoromethylstyrene and 2.16 grams of 2,3-dihydroxy-1-propanethiol.

EXAMPLE 22

3-Methylthio-1-methyl-5-(3-trifluoromethylphenyl)-4(1H)-pyridone, 2.15 grams from 7.4 grams of α-bromoacetyl-β-diethylamino-3-trifluoromethylstyrene and an excess of methyl mercaptan, m.p. 121°–122° C.

EXAMPLE 23

3-n-Propylthio-1-methyl-5-(3-trifluoromethylphenyl)-4(1H)-pyridone, 2.55 grams from 7.24 grams of α-bromoacetyl-β-diethylamino-3-trifluoromethylstyrene and 1.6 grams of 1-propanethiol, m.p. 101°–102° C.

EXAMPLE 24

3-Isopropylthio-1-methyl-5-(3-trifluoromethylphenyl)-4(1H)-pyridone, 2.1 grams from 7.24 grams of α-bromoacetyl-β-diethylamino-3-trifluoromethylstyrene and 1.6 grams of 2-propanethiol, m.p. 93°–94° C.

EXAMPLE 25

3-n-Butylthio-1-methyl-5-(3-trifluoromethylphenyl)-4(1H)-pyridone, 2.43 grams from 7.24 grams of α-bromoacetyl-β-diethylamino-3-trifluoromethylstyrene and 2.0 grams of 1-butanethiol, m.p. 109°–110° C.

I claim:

1. A method for the preparation of a substituted pyridone having the formula

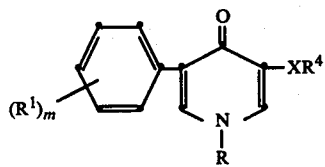

which comprises:

(a) treating an enamine having the formula

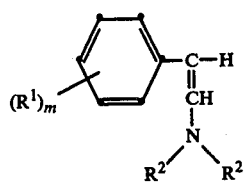

with bromoacetyl bromide in the presence of an acid scavenger in an inert solvent at a temperature of from about −25° C. to about 50° C. to form an α-bromoacetyl-β-aminostyrene having the formula

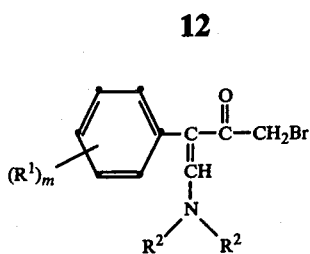

(b) treating the α-bromoacetyl-β-aminostyrene with an anion represented by $$(-)XR^4 \qquad (IV)$$

in an inert solvent at a temperature of from about 0° C. to about 100° C. to give an α-substituted acetyl-β-aminostyrene having the formula

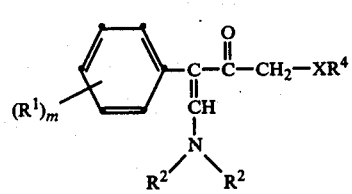

(c) formylating or aminoformylating the α-substituted acetyl-β-aminostyrene by treatment with
  (1) a $C_1$–$C_2$ alkyl formate and an alkali metal $C_1$–$C_2$ alkoxide in an aprotic solvent at a temperature of from about −25° C. to about 25° C., or
  (2) an N,N-dimethylformamide acetal at a temperature within the range of from about 50° C. to about 150° C., and treating with an amine, $RNH_2$, in a protic solvent at a temperature of from about −20° C. to about 100° C. to produce the substituted pyridone;

wherein R represents
$C_1$–$C_3$ alkyl,
$C_1$–$C_3$ alkyl substituted with halo, cyano, carboxy, or methoxycarbonyl,
$C_2$–$C_3$ alkenyl,
$C_2$–$C_3$ alkynyl,
$C_1$–$C_3$ alkoxy,
acetoxy, or
dimethylamino, provided that R comprises no more than 3 carbon atoms; each $R^1$ independently represents
halo,
$C_1$–$C_8$ alkyl,
$C_1$–$C_8$ alkyl substituted with halo,
$C_1$–$C_8$ alkyl monosubstituted with phenyl, cyano, or $C_1$–$C_3$ alkoxy,
$C_2$–$C_8$ alkenyl,
$C_2$–$C_8$ alkenyl substituted with halo,
$C_2$–$C_8$ alkynyl,
$C_2$–$C_8$ alkynyl substituted with halo,
$C_3$–$C_6$ cycloalkyl,
$C_4$–$C_6$ cycloalkenyl,
$C_4$–$C_8$ cycloalkylalkyl,
$C_1$–$C_3$ alkanoyloxy,
$C_1$–$C_3$ alkylsulfonyloxy,
phenyl,
phenyl monosubstituted with halo, $C_1$–$C_3$ alkyl, $C_1$–$C_3$ alkoxy, or nitro,
nitro,
cyano,
carboxy, hydroxy,
$C_1$–$C_3$ alkoxycarbonyl,
—O—$R^3$,
—S—$R^3$,
—SO—$R^3$, or
—$SO_2$—$R^3$;
$R^3$ represents
   $C_1$–$C_{12}$ alkyl,
   $C_1$–$C_{12}$ alkyl substituted with halo,
   $C_1$–$C_{12}$ alkyl monosubstituted with phenyl, cyano, or $C_1$–$C_3$ alkoxy,
phenyl,
phenyl monosubstituted with halo, $C_1$–$C_3$ alkyl, $C_1$–$C_3$ alkoxy or nitro,
$C_3$–$C_6$ cycloalkyl,
$C_4$–$C_8$ cycloalkylalkyl,
$C_2$–$C_{12}$ alkenyl,
$C_2$–$C_{12}$ alkenyl substituted with halo,
$C_2$–$C_{12}$ alkynyl,
$C_2$–$C_{12}$ alkynyl substituted with halo,
provided that $R^3$ comprises no more than 12 carbon atoms; each $R^2$ independently represents $C_1$–$C_4$ alkyl or both $R^2$ groups taken together with the nitrogen atom to which they are attached represent pyrrolidino, piperidino, or morpholino;
$R^4$ represents
   $C_1$–$C_6$ alkyl,
   $C_1$–$C_6$ alkyl substituted with halo,
   $C_1$–$C_6$ alkyl mono- or disubstituted with hydroxy, $CH_2R^5$,
   benzyl,
   phenyl or
   phenyl substituted with halo, $C_1$–$C_3$ alkyl, halo $C_1$–$C_3$ alkyl or $C_1$–$C_3$ alkoxy;
$R^5$ represents
   $C_2$–$C_5$ alkenyl,
   $C_2$–$C_5$ alkenyl substituted with halo or
   $C_2$–$C_5$ alkynyl;
X represents oxygen or sulfur; and
$m$ represents 0, 1 or 2.

2. A method as in claim 1 wherein X is sulfur.
3. A method as in claim 2 wherein $R^4$ is $C_1$–$C_6$ alkyl.
4. A method as in claim 1 wherein R is methyl.
5. A method as in claim 1 wherein $R^1$ is 3-trifluoromethyl and $m$ is 1.
6. A method as in claim 1 wherein $R^4$ is ethyl.